US006670433B2

(12) United States Patent
McLain et al.

(10) Patent No.: US 6,670,433 B2
(45) Date of Patent: Dec. 30, 2003

(54) POLYMERS OF SUBSTITUTED CYCLOPENTENES

(75) Inventors: Stephan James McLain, Wilmington, DE (US); Elizabeth Forrester McCord, Hockessin, DE (US); Alison Margaret Anne Bennett, Wilmington, DE (US); Steven Dale Ittel, Wilmington, DE (US); Karl Jeffrey Sweetman, Wilmington, DE (US); Mark F. Teasley, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 224 days.

(21) Appl. No.: 09/824,461

(22) Filed: Apr. 2, 2001

(65) Prior Publication Data

US 2003/0055186 A1 Mar. 20, 2003

Related U.S. Application Data

(62) Division of application No. 09/277,095, filed on Mar. 26, 1999, now Pat. No. 6,258,908.
(60) Provisional application No. 60/079,733, filed on Mar. 27, 1998.

(51) Int. Cl.[7] .................................................. C08F 4/42
(52) U.S. Cl. ..................... 526/161; 526/308; 526/169.1; 526/217; 526/236; 526/133; 526/141; 502/200; 502/229

(58) Field of Search ............................... 526/308, 169.1, 526/217, 236, 161, 133, 141; 502/200, 229

(56) References Cited

U.S. PATENT DOCUMENTS

| 3,505,301 A | | 4/1970 | Natta et al. |
| 5,204,429 A | | 4/1993 | Kaminsky et al. |
| 5,635,573 A | | 6/1997 | Harrington et al. |
| 5,852,145 A | * | 12/1998 | McLain et al. ............. 526/133 |
| 5,880,241 A | | 3/1999 | Brookhart et al. |

FOREIGN PATENT DOCUMENTS

| EP | 0 304 671 | 3/1998 |
| EP | 0 884 331 A2 | 12/1998 |
| WO | WO 98/56832 | 12/1998 |

OTHER PUBLICATIONS

Boor, J. et al., Polymerization of Cyclopenetene, 3–Methylcyclopentene, and 3–Methylcyclohexene, *Die Makromolekulare Chemie*, 1966, 26–37, 90.
PCT International Search Report dated Nov. 18, 1999 for PCT/US99/06458.

* cited by examiner

*Primary Examiner*—Ling-Siu Choi

(57) ABSTRACT

Substituted cyclopentenes, such as alkyl cyclopentenes, are polymerized by selected α-imine complexes of nickel and palladium. The polymers are useful as molding resins or elastomers. Also disclosed herein are novel catalysts for the polymerization of cyclopentenes to form novel higher melting homopolycyclopentenes.

1 Claim, No Drawings

POLYMERS OF SUBSTITUTED CYCLOPENTENES

This application is a divisional application Ser. No. 09/277,095 (filed Mar. 26, 1999), now U.S. Pat. No. 6,258,908 which claims priority from U.S. provisional Application Ser. No. 60/079,733 (filed Mar. 27, 1998), which is incorporated by reference herein for all purposes as if fully set forth.

FIELD OF THE INVENTION

Cyclopentenes which are substituted with various hydrocarbyl groups can be homopolymerized or copolymerized with cyclopentene itself to form polymers useful as molding resins. Nickel and palladium α-diimine complexes can be used as catalysts for these polymerizations, but also disclosed herein are α-diimine complexes which are novel catalysts for the polymerization of cyclopentenes.

TECHNICAL BACKGROUND

Nickel and palladium α-diimine complexes are known catalysts for the polymerization of various olefins, including cyclopentene itself, see for instance World Patent Application 96/23010. However, methods for polymerization of various substituted cyclopentenes have not been reported with such catalysts.

Homopolymers of 3-methylcyclopentene have been reported, see for instance J. Boor, et al., Die Makromolekulare Chemie, vol. 90, p. 26–37 (1966).

World Patent Applications 96/23010 and 98/27124, and U.S. Pat. No. 5,880,241 describe homopolycyclopentenes which are melt processable.

SUMMARY OF THE INVENTION

This invention concerns a polymer, comprising, repeat units derived from one or more of 3-methylcyclopentene, 4-methylcyclopentene, 3-ethylcyclopentene or 3-cyclopentylcyclopentene, and optionally cyclopentene, provided that when said polymer is a homopolymer of 3-methylcyclopentene, at least about 40 mole percent of repeat units present are of the formula

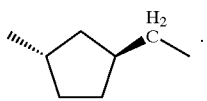

(II)

This invention also concerns a process for the polymerization of one or more olefins selected from the group consisting of 3-methylcyclopentene, 4-methylcyclopentene, 3-ethylcyclopetnene and 3-cyclopentylcyclopentene, and optionally cyclopentene, by contacting, at a temperature of −100° C. to about +200° C., said olefin with a olefin polymerization catalyst system containing a nickel or palladium complex of a compound of the formula

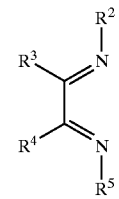

and optionally other cocatalysts, wherein $R^2$ and $R^5$ are each independently hydrocarbyl or substituted hydrocarbyl, provided that the carbon atom bound to the imino nitrogen atom has at least two carbon atoms bound to it; and $R^3$ and $R^4$ are each independently hydrogen, hydrocarbyl, substituted hydrocarbyl, or $R^3$ and $R^4$ taken together are hydrocarbylene or substituted hydrocarbylene to form a carbocyclic ring.

Disclosed herein is a compound of the formula

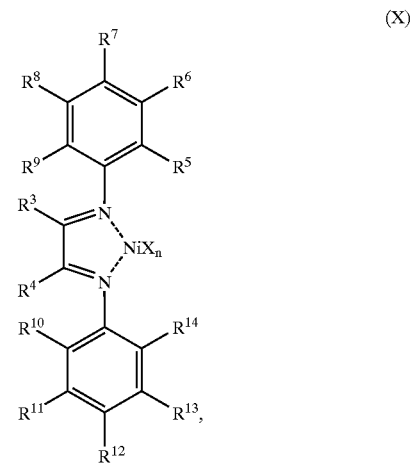

(X)

wherein:
each X is independently an anion;
n is 2 or 3;
$R^3$ and $R^4$ taken together are

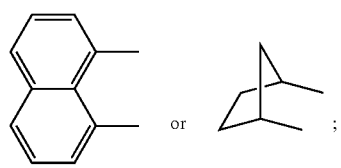

$R^5$, $R^6$, $R^7$, $R^8$, $R^9$, $R^{10}$, $R^{11}$, $R^{12}$, $R^{13}$, and $R^{14}$ are each independently hydrogen, hydrocarbyl, substituted hydrocarbyl or a functional group;
and provided that:
when $R^5$ is the same as $R^{10}$, and $R^9$ is the same as $R^{14}$, said compound is in an anti form;
no more than one of $R^5$, $R^9$, $R^{10}$, and $R^{14}$ is hydrogen;
any two of $R^5$, $R^6$, $R^7$, $R^8$, $R^9$, $R^{10}$, $R^{11}$, $R^{12}$, $R^{13}$, and $R^{14}$ vicinal to one another may form a ring; and
$R^5$ is different than $R^9$.

This invention also concerns a process for the polymerization of one or more of cyclopentene and a substituted cyclopentene, comprising, contacting, at a temperature of −100° C. to about +200° C., said olefin with a olefin polymerization catalyst system containing a compound of the formula

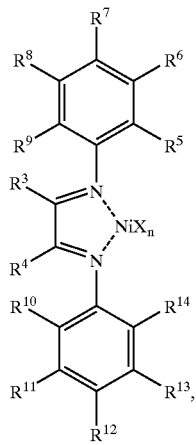

(X)

and optionally cocatalysts, wherein:
  each X is independently a monoanion;
  n is 2 or 3;
  $R^3$ and $R^4$ taken together are

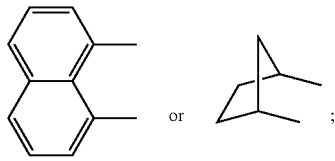

$R^5$, $R^6$, $R^7$, $R^8$, $R^9$, $R^{10}$, $R^{11}$, $R^{12}$, $R^{13}$, and $R^{14}$ are each independently hydrogen, hydrocarbyl, substituted hydrocarbyl or a functional group;
  and provided that:
    when $R^5$ is the same as $R^{10}$, and $R^9$ is the same as $R^{14}$, said compound is in an anti form;
    no more than one of $R^5$, $R^9$, $R^{10}$, and $R^{14}$ is hydrogen;
    any two of $R^5$, $R^6$, $R^7$, $R^8$, $R^9$, $R^{10}$, $R^{11}$, $R^{12}$, $R^{13}$, and $R^{14}$ vicinal to one another may form a ring; and
    $R^5$ is different than $R^9$.

This invention also concerns a homopolycyclopentene that has an end of melting point of 325° C. to about 380° C.

DETAILS OF THE INVENTION

Herein certain terms are used to define certain chemical groups or compounds. These terms are defined below.

A "hydrocarbyl group" is a univalent group containing only carbon and hydrogen. If not otherwise stated, it is preferred that hydrocarbyl groups herein contain 1 to about 30 carbon atoms.

By "substituted hydrocarbyl" herein is meant a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings.

By an alkyl aluminum compound is meant a compound in which at least one alkyl group is bound to an aluminum atom. Other groups such as alkoxide, oxygen, and halogen may also be bound to aluminum atoms in the compound.

By "hydrocarbylene" herein is meant a divalent group containing only carbon and hydrogen. Typical hydrocarbylene groups are —$(CH_2)_4$—, —$CH_2CH(CH_2CH_3)CH_2CH_2$— and

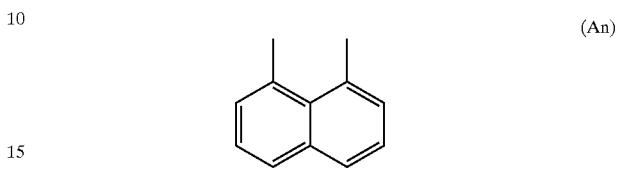

(An)

If not otherwise stated, it is preferred that hydrocarbylene groups herein contain 1 to about 30 carbon atoms.

By "substituted hydrocarbylene" herein is meant a hydrocarbylene group which contains one or more substituent groups which are inert under the process conditions to which the compound containing these groups is subjected. All of the hydrogen atoms may be substituted, as in trifluoromethyl. The substituent groups also do not substantially interfere with the process. If not otherwise stated, it is preferred that substituted hydrocarbylene groups herein contain 1 to about 30 carbon atoms. Included within the meaning of "substituted" are heteroaromatic rings.

By an (inert) functional groups is meant a functional group that does not substantially interfere with the utility of the compound in which that group is located and does not make that compound unstable to the point where it is not useful for its intended purpose. Useful functional groups include halo and ether.

By "anti" herein is meant that when $R^5$ is identical to $R^{10}$, and $R^9$ is identical to $R^{14}$, the identical groups (i.e., the pairs $R^5$ and $R^{10}$, and $R^9$ and $R^{14}$ are on opposite sides of the approximate plane formed by the two carbons and the two nitrogen atoms of the α-diimine grouping and the nickel atom.

In the polymerization process described herein for the substituted cyclopentenes (SCP) using α-diimine complexes of nickel or palladium, the same catalysts compounds and systems and conditions as reported in World Patent Application 96/23010, which is hereby included by reference, are used. Preferred nickel and palladium complexes reported therein, especially those preferred for the polymerization of cyclopentene itself, are preferred for the polymerization of the SCP reported herein. Likewise, preferred conditions, such as temperature and solvent (if used) are also preferred herein. A preferred cocatalysts, as in WO 96/23010 is an alkyl aluminum compound.

The various SCP reported herein polymerize to form one or more "unusual" repeat units in the resulting polymer. Rarely if at all does any of the SCP polymerize into the polymer merely by adding across the double bond present in the cyclopentyl ring. Also, there may be a difference between repeat structures obtained using nickel and palladium complexes. The structures of various polymers are described below.

3- and 4-Methylcyclopentene with Pd Catalyst (see Examples 4, 5 and 8). These two monomers give almost identical polymers with Pd catalysts. The majority of the repeat units are 1,3'-trans of the formula

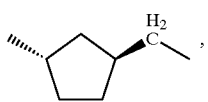
(II)

typically about 80 mole percent of the repeat units. 1,2'-Trans units,

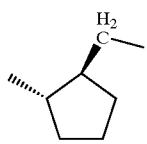
(III)

are also present in minor amounts, typically about 10–25 mole percent of the repeat units. There may also be small amounts of repeat units containing pendant methyl groups, especially from 4-methylcyclopentene.

3-Methylcyclopentene with Ni Catalyst (Example 6). This polymerization gives polymers with substantial amounts (preferably >40 mole percent, and typically 60 mole percent) of repeat units of the formula (II). Also present are a substantial amount of repeat unit (IX), typically about 40 mole percent of the repeat units.

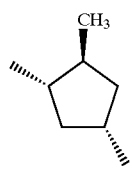
(IX)

4-Methylcyclopentene and Ni Catalyst (Example 13). This gives a polymer containing substantial amounts of repeat units (II) and (IX), typically about 50 mole percent of each.

3-Ethylcyclopentene with Pd Catalyst (Example 9). This polymer has two predominant structures, 1,3'-trans (IV), and 1,2'-trans (V),

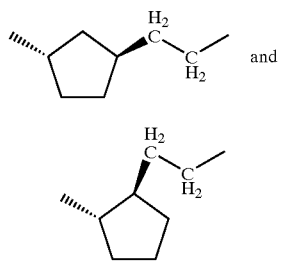
(IV) and (V)

The majority of the repeat units, typically about 75 mole percent are (IV), while a minority, usually a substantial amount, of the repeat units are (V), typically about 25 mole percent.

3-Ethylcyclopentene with Ni Catalyst (Example 12). Structures believed to be present in substantial amounts include (IV) and (VI). Typically (IV) is a majority of the repeat units, often about 70 mole percent, while (VI) is typically about 30 mole percent of the repeat units.

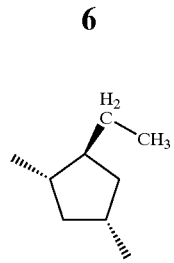
(VI)

Cyclopentylcylopentene with Ni Catalyst (Example 2). In this polymer, trans 1,3-cyclopentyl, (VII), is a majority of the repeat unit of the polymer, typically about 80 mole percent, while cis-1,3 enchainment (VIII) is a minor, but usually substantial, portion of the repeat units, typically about 20 mole percent.

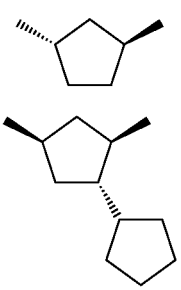
(VII)

(VIII)

By a "substantial" amount of repeat units herein in any particular polymer is meant at least 10 mole percent of the repeat units.

The homo- and copolymers described herein are useful as thermoplastic molding resins (for those that are crystalline or glassy at ambient conditions) or as elastomers (for those which are rubbery at ambient conditions). In copolymers with cyclopentene, the use of the substituted cyclopentenes allows lowering of the melting point of the polymer, when compared to homopolycyclopentene.

It has been found that in complexes like (X), when none of $R^5$, $R^9$, $R^{10}$, and $R^{14}$ are hydrogen, rotation about the C—N bond of the aryl groups is hindered. Therefore, when $R^5$ is the same as $R^{10}$, and $R^9$ is the same as $R^{14}$ the complex can exist and be isolated as either syn or anti isomers. (X) is the anti form of the compound. It is preferred that $R^5$, $R^9$, $R^{10}$, and $R^{14}$ are hydrocarbyl, substituted hydrocarbyl, or halo. In another preferred embodiment, $R^5$, $R^9$, $R^{10}$, and $R^{14}$ are all alkyl and it is more preferred that $R^5$ and $R^{10}$ are methyl, and $R^9$ and $R^{14}$ are identical alkyl groups having 2 or more carbons, especially preferably $R^9$ and $R^{14}$ are isopropyl. It is also preferred that X is halide and/or n is 2. It is also preferred that in (X) $R^3$ and $R^4$ taken together are (An).

(X) can be made by methods described in World Patent Application 96/23010. The anti isomer may be isolated by fractional crystallization.

In the polymerization process described herein using (X), the same catalyst system and conditions as reported in World Patent Application 96/23010 for α-diimine complexes, which is hereby included by reference, are used. Preferred structures are also reported therein, especially those preferred for the polymerization of cyclopentene itself, and are also preferred for the polymerization using (X). Likewise, preferred conditions, such as temperature and solvent (if used) are also preferred herein. A preferred cocatalyst, as in WO 96/23010 is an alkyl aluminum compound.

Compounds such as (X), when polymerizing cyclopentene, give a polymer which has properties that are often different from those polymers obtained with other α-diimine nickel complexes. For example, at equivalent conditions, the melting point tends to be somewhat higher. This is believed to be due to a different mechanism of stereoregulation by these complexes compared to other nickel α-diimine complexes. Other α-diimine nickel complexes produce partially isotactic polycyclopentene by a chain end control mechanism. (Stephan J. McLain et. al., Macromolecules, Volume 31, Number 19, pages 6705–6707, 1998). By studying the hydrooligomerization reaction by the method described in this reference, we have found that surprisingly, compounds (X) give enantiosite control of the polymerization instead of the chain-end control of stereochemistry observed with α-diimine Ni complexes. We believe this mechanism of stereocontrol produces longer isotactic segments in the partially isotactic polymer, thus leading to higher melting points. If the polymerization temperature is raised, the melting point of polycyclopentene made by any α-diimine nickel complex will usually decrease. It is usually desirable to run polymerizations at higher temperatures because the rates usually increase with temperature. Thus a balance often needs to be struck between polymerization rate and polymer melting point. An advantage of (X) when $R^3$ and $R^4$ taken together are (An) is that it can be used at a higher polymerization temperature and still produce a polymer with a relatively high melting point, although the polymer will have a melting point that is lower than obtained at lower reaction temperatures.

In the Examples, the following convention is used for naming α-diimine complexes of metals, and the α-diimine itself. The α-diimine is indicated by the letters "DAB". To the left of the "DAB" are the two groups attached to the nitrogen atoms, herein often called $R^2$ and $R^5$. To the right of the "DAB" are the groups on the two carbon atoms of the α-diimine group, herein usually termed $R^3$ and $R^4$. To the right of all this appears the metal, ligands attached to the metal and finally any anions (X).

In the Examples the following abbreviations are used:
3-EtCyp—3-ethylcyclopentene
3-MeCyp—3-methylcyclopentene
4-MeCyp—4-methylcyclopentene
BAF—tetrakis[3,5-bis(trifluoromethyl)phenyl]borate
DSC: Differential Scanning Calorimetry
$H_f$—heat of fusion (melting)
MeOH—Methanol
PMAO—polymethylaluminoxane
RT—room temperature
TCB—1,2,4-trichlorobenzene
Tg—glass transition temperature
TGA—thermogravimetric analysis
Tm—melting point NMR Techniques The following describes generally some of the techniques used in determining the structures of the polymers described herein.
INADEQUATE (Incredible Natural Abundance DoublE QUAntum Transfer Experiment):
  This 2D NMR technique gives information on connectivities between carbon atoms. The 2D contour map shows correlations between carbons and their double quantum frequencies. Carbons which share the same double quantum frequency (have correlations on the same ROW of the 2D plot) are connected by covalent bonds. This is a $^{13}C$ observe experiment with VERY LOW signal to noise, and can take 4 days per sample.

HMQC (Heteronuclear Multiple Quantum Coherence):
  This 2D NMR technique gives information on connectivities between carbons and protons that are directly bonded to each other. The correlations in the 2D contour plot connect each proton signal with the carbon signal for the carbon covalently bonded to that proton. This is a high signal-to-noise very quick $^1H$ NMR observe experiment. The digital resolution is best in the $^1H$ dimension.
HSQC (Heteronuclear Single Quantum Coherence):
  The 2D NMR experiment gives basically the same results as the HMQC experiment, but is sometimes better for polymers which have shorter relaxation time constants.
HETCOR (HETeronuclear CORrelation):
  This 2D NMR technique gives information on connectivities between carbons and protons that are directly bonded to each other. The correlations in the 2D contour plot connect each carbon signal with the proton signal for the proton covalently bonded to that carbon. This is a low signal-to-noise $^{13}C$ observe experiment. The digital resolution is best in the $^{13}C$ dimension.
HMBC (Heteronuclear Multiple Bond Correlation):
  This 2D NMR technique gives information on connectivities between carbons and protons that are separated by two and/or three covalent bonds. The correlations in the 2D contour plot connect each proton signal with the carbon signal for the carbons that are two and/or three bonds separated from that proton. This is a medium signal-to-noise $^1H$ NMR observe experiment and requires magnetic field gradients to be really successful. The digital resolution is best in the $^1H$ dimension. The carbon does not need to carry a proton making this a useful adjunct to the HMQC-TOCSY experiment.
TOCSY TOtal Correlation SpectroscopY):
  This 2D NMR technique gives information on all the protons in a particular neighborhood. How big the neighborhood is depends on the length of the NMR spin lock that is used in the experiment, and can be adjusted. The neighborhood encompasses a group of protons that are pairwise on neighboring carbons and are pairwise spin coupled to each other. A quaternary carbon, ether, carbonyl, etc., interrupts the chain of protons on neighboring carbons and limits the neighborhood. This is a high signal to noise $^1H$ observe experiment.
HMQC-TOCSY (or HSQC-TOCSY)
  This experiment combines the HMQC (or HSQC) and TOCSY experiments together. The result is that each proton shows correlations to all the protonated carbons in its neighborhood, thus defining a GROUP of carbons that are pairwise covalently bonded. This is a medium signal-to-noise $^1H$ NMR observe experiment. The digital resolution is best in the $^1H$ dimension. This is one of the most useful experiments as it groups both the protons and carbons that belong in a particular area or microstructure of the polymer.
COSY (COrrelation SpectroscopY):
  This 2D NMR technique gives information on protons that are spin coupled to each other, generally on neighboring carbons or 4 bonds apart. This is a high signal-to-noise very quick $^1H$ NMR observe experiment.
DEPT (Distortionless Enhancement by Polarization Transfer):
  This 1 D multipulse NMR experiment gives information on the number of protons attached to each carbon atom. Carbons with one or three protons attached are positive, carbons with two protons attached are negative, and carbons without any protons are not observed in this experiment. This is a $^{13}C$ observed experiment, but the signal to noise is very high because magnetization is transferred from the protons and because the scans can be repeated according to the proton (not the carbon, which is slower) relaxation time.

Melting Points

The melting point of the polymers, particularly homopolycyclopentene, are determined by Differential Scanning Calorimetry at a heating rate of 15° C./min (except as otherwise noted, but this rate is the rate applicable in the claims—lower heating rates tend to give somewhat lower melting points, and higher heating rates tend to give somewhat lower melting points), and taking the maximum of the melting endotherm as the melting point. However these polymers tend to have relatively diffuse melting points, so it is preferred to measure the "melting point" by the end of melting point. The method is the same, except the end of melting is taken as the end (high temperature end) of the melting endotherm which is taken as the point at which the DSC signal returns to the original (extrapolated) baseline. If not stated as an end of melting point the melting point has been taken as the peak of the melting endotherm.

Monomer Sources

3-Methylcyclopentene (3-MeCyp); prepared according to Nugent et. al. (J. Am. Chem. Soc., 1995, vol. 117, p. 8992) was degassed and stored in a drybox over 5 Å molecular sieves.

3-Ethylcyclopentene (3-EtCyp) (Wiley Organics, 99%) was degassed and taken into a nitrogen purged drybox. It was then run through alumina and stored over 5 Å molecular sieves.

4-Methylcyclopentene (4-MeCyp) (Carnagie Mellon University-American Petroleum Institute standards) was used as received.

Cyclopentylcylopentene was obtained from Chemsampco.

EXAMPLE 1

Preparation of Poly(cyclopentene-co-3-Ethylcyclopentene)

In a dry box, to an oven dried scintillation vial, were added in order: (XIII) (0.04 g, 0.06 mmol); tris (perfluorophenyl)borane (0.094 g, 0.184 mmol); cyclopentene (2.08 g, 30.5 mmol); 3-ethylcyclopentene (2.92 g, 30.4 mmol) and then triethylaluminum (1.0 M in hexanes, 183 µl, 0.183 mmol). The reaction exothermed initially and the viscosity increased within one h. The reaction was mixed on the IKA Vibrax-VXR® mixer for 17 h total after which time a solution of toluene (8 ml) and 8-hydroxyquinoline (0.05 g, 0.34 mmol) was added and the mixture was allowed to stand overnight. The mixture was removed from the scintillation vial and stirred with an additional 30 ml of toluene to completely dissolution in a small Erlenmeyer flask for 2 h. The mixture was then precipitated into 500 ml of MeOH, filtered, washed with MeOH and dried on the vacuum line at 110° C. for 4 h. Net wt=2.87 g. By DSC (heating rate of 30° C./min) the polymer had a Tg at 58° C. and no melting transition.

EXAMPLE 2

Preparation of Poly(3-Cyclopentycyclopentene)

In a dry box, to an oven dried scintillation vial, were added in order: (XIII) (0.024 g, 0.036 mmol); tris (perfluorophenyl)borane (0.056 g, 0.109 mmol); 3-cyclopentylcyclopentene (2.46 g, 18.1 mmol) and then triethylaluminum (1.0 M in hexanes 109 µl, 0.109 mmol) The reaction was mixed on the IKA-Vibrax-VXR® vibramixer for 70 h, at the end of which the reaction mixture was immobile. At 70 h, 8-hydroxyquinoline (0.106 g, 0.726 mmol) and toluene (8.8 ml) were added to quench the reaction and mixed for 2 h. Not all of the polymer dissolved during this period. The reaction was dumped into 50 ml of stirred MeOH, filtered and washed with 3×20 ml of fresh MeOH. This polymer was then re-dissolved in 20 ml of chlorobenzene at 120° C. and reverse precipitated upon cooling by the slow addition of MeOH (60 ml) to the stirred solution of polymer. The polymer precipitated as a blob. The cloudy supernatant was decanted and the elastomeric solid was slurried and kneaded in 3 portion (15 ml) each of MeOH. The wash supernatant was decanted off the polymer following each kneading. The polymer was dried overnight in the dry box antechamber and then at 125° C. on a vacuum line for 4 h. Net wt.=1.17 g. By DSC (heating rate 30° C./min) the polymer had a Tg of 70° C.

EXAMPLE 3

Preparation of Poly(Cyclopentene-co-3-ethylcyclopentene)

In a dry box, to an oven dried scintillation vial, were added in order: (XIII) (0.0095 g, 0.014 mmol); tris (perfluorophenyl)borane (0.022 g, 0.043 mmol); cyclopentene (9.34 g 137 mmol); 3-ethylcyclopentene (0.66 g, 6.86 mmol) and then triethylaluminum (1.0 M in hexanes, 43 µl, 0.043 mmol). The reaction was mixed on the IKA-Vibrax-VXR® vibramixer for 96 h after which methylene chloride (1 ml) and 8-hydroxyquinoline (0.043 g, 0.29 mmol) were added to quench the reaction. The reaction was then poured into 50 ml of stirred MeOH, filtered and washed with 3×20 ml of MeOH. The solid was dried overnight at 120° C. in a vacuum oven with a slow nitrogen bleed. Net wt.=1.53 g.

EXAMPLE 4

3-Methylcyclopentene Polymerization with Pd Catalyst

Inside a nitrogen purged drybox, the palladium catalyst, {[(2,6-iPr$_2$Ph)$_2$DABMe$_2$]Pd(CH$_2$CH$_2$CH$_2$CO$_2$Me)}BAF (46 mg, 0.031 mmol), was dissolved in 1 ml anhydrous CH$_2$Cl$_2$. 3-MeCyp (1 ml) was added and the resulting solution allowed to stir for 7 days over which time it gradually darkened. The volatile solvent and unreacted monomer were removed and the resulting sticky polymer was washed with MeOH and dried. Tg=10° C. (DSC)

EXAMPLE 5

3-MeCyp Polymerized with a Pd Catalyst

Inside a nitrogen purged drybox, the palladium catalyst, {[(2,6-iPr$_2$Ph)$_2$DABMe$_2$]Pd(CH$_2$CH$_2$CH$_2$CO$_2$Me)}BAF (0.020 g, 0.014 mmol), was dissolved in anhydrous CH$_2$Cl$_2$ (1 ml) and 3-MeCyp (1.25 ml) was added. The resulting solution was stirred for 2 h after which it had become viscous. After 4 h it had solidified and stopped stirring. The solution was allowed to react for a further 5 days after which the solvent and volatiles were removed and the resulting foam dried under vacuum overnight. Yield=0.72 g.

EXAMPLE 6

3-MeCyp Polymerized with a Ni Catalyst

Inside a nitrogen purged drybox, the nickel catalyst, [(2,4,6-Me$_3$Ph)$_2$DABAN]NiBr$_2$ (0.010 g, 0.015 mmol) was placed in anhydrous toluene (1 ml) and 3-MeCyp (1.25 ml) added. PMAO (1.1 ml, 9.8 wt % Al in toluene, Akzo) was added with stirring and the resulting deep purple solution was stirred for 5 days. It was then removed from the drybox and MeOH/10%HCl added. The sticky polymer precipitated and the solvents were decanted. The polymer was washed repeatedly with MeOH with stirring until a fine powder formed. This was filtered and washed and dried.

EXAMPLE 7

Cyclopentene/3-Methylcyclopentene Copolymer

Inside a nitrogen purged drybox, the palladium catalyst, {[(2,6-iPr$_2$Ph)$_2$DABMe$_2$]Pd(CH$_2$CH$_2$CH$_2$CO$_2$Me)}BAF (77 mg, 0.053 mmol) was dissolved in CH$_2$Cl$_2$ (2 ml) and cyclopentene (2 ml) and 3-MeCyp (1 ml) added. The solution was stirred for 4 days after which the volatiles were removed. MeOH was added and the polymer filtered, washed well with MeOH and finally with 2% Irganox® 1010/acetone solution and dried. Yield=1.06 g. Tm (DSC)= 210.5° C., Tg (DSC)=73° C. $^{13}$C-NMR (TCB, 120° C.) indicated ~5% 3-MeCyp incorporation.

EXAMPLE 8

4-Methylcyclopentene Polymerization with Pd Catalyst

Inside a nitrogen purged drybox, the palladium catalyst {[(2,6-iPr$_2$Ph)$_2$DABMe$_2$]Pd(CH$_2$CH$_2$CH$_2$CO$_2$Me)}BAF (20 mg, 0.031 mmol) was dissolved in 1 ml CH$_2$Cl$_2$. 4-MeCyp (1 ml) was added and the resulting solution allowed to stir for 5 days over which time it gradually darkened. The volatile solvent and unreacted monomer were removed resulting in a sticky orange foam (0.25 g).

EXAMPLE 9

3-Ethylcyclopentene Polymerized with a Pd Catalyst

Inside a drybox, the palladium catalyst, {[(2,6-iPr$_2$Ph)$_2$DABMe$_2$]Pd(CH$_2$CH$_2$CH$_2$CO$_2$Me)}BAF (24 mg, 0.016 mmol) was dissolved in anhydrous dichloroethane (2 ml) and 3-EtCyp (1.58 g) was added. The orange solution was stirred at room temperature and after 12 h had solidified. After 8 days the volatiles were removed. The polymer was removed from the drybox and MeOH was added and the polymer filtered, washed well with MeOH and finally with 2% Irganox® 1010/acetone solution and dried. Yield=1.06 g. No crystallinity was observed in the DSC analysis.

EXAMPLE 10

3-Ethylcyclopentene Polymerized with a Ni Catalyst

Inside a drybox, the nickel catalyst, [(2-PhPh)$_2$DABMe$_2$]NiBr$_2$ (10.8 mg, 0.018 mmol) was placed in anhydrous toluene (2 ml) and 3-EtCyp (1.72 g) was added. PMAO (0.5 ml, 9.8 wt % Al in toluene, Akzo) was added with stirring and the resulting deep purple solution was stirred for 8 days. It was then removed from the drybox and MeOH/10%HCl added. The organic layer was isolated and the volatiles removed. This was washed successive times with MeOH and then dried. Yield=0.43 g of a viscous oil.

EXAMPLE 11

3-Ethylcyclopentene Polymerized with a Ni Catalyst

Inside a drybox, the nickel catalyst, [(2,4,6-Me$_3$Ph)$_2$DABAN]NiBr$_2$ (16.5 mg, 0.026 mmol) was placed in a glass vial and 3-EtCyp (2.5 g) was added. B(C$_6$F$_5$)$_3$ (40 mg, 0.08 mmol) and AlEt$_3$ (0.08 ml, 0.08 mmol) were added with stirring and the resulting deep purple solution was stirred for 8 days. At this time it was solidified. It was removed from the drybox and dissolved in CH$_2$Cl$_2$ and precipitated by addition to MeOH. The product was filtered, washed well with MeOH and dried under vacuum. Yield=2.27 g. TGA shows no weight loss up to 400° C. Tg (DSC) 11.3° C. No melting point was observed by DSC.

EXAMPLE 12

3-Ethylcyclopentene Polymerization with a Ni Catalyst

Inside a drybox, the nickel catalyst, [(2-PhPh)$_2$DABMe$_2$]NiBr$_2$ (15.8 mg, 0.026 mmol) was placed in a glass vial and 3-EtCyp (2.5 g) was added. B(C$_6$F$_5$)$_3$ (40 mg, 0.08 mmol) and AlEt$_3$ (0.08 ml, 0.08 mmol) were added with stirring and the resulting deep brown solution was stirred for 8 days. At this time it was viscous. It was removed from the drybox, dissolved in CH$_2$Cl$_2$ and precipitated by addition to MeOH. The liquid was decanted and washed repeatedly in this way with MeOH and finally dried under vacuum. Yield=1.83 g viscous oily polymer. TGA shows no weight loss up to 350° C. Tg (DSC) 1.9° C. No melting point was observed by DSC.

EXAMPLE 13

4-Methylcyclopentene Polymerized with a Ni Catalyst

Inside a drybox, the nickel catalyst, [(2,4,6-Me$_3$Ph)$_2$DABAN]NiBr$_2$ (9.8 mg, 0.015 mmol) was placed in a glass vial with anhydrous toluene (2 ml) and 4-MeCyp (1 ml) was added. PMAO-IP (0.8 ml, 12.8 wt % Al in toluene, Akzo) was added with stirring and the resulting deep purple solution was stirred for 10 days. At this time it was viscous. It was removed from the drybox and MeOH/10% HCl was added to precipitate the polymer. It was then redissolved in CHCl$_3$ and precipitated by addition to MeOH. The product was filtered, washed well with MeOH and dried under vacuum. Yield=0.41 g white solid. Tg (DSC)=40.8° C. No melting point was observed in the DSC.

EXAMPLE 14

To a 3-necked 250 RBF equipped with a condenser, stoppers and a magnetic stir bar is charged (3.0 g, 16 mmol) of acenapthenequinone, (5.6 g, 38 mmol) of 2-methyl-6-isopropylaniline and 40 ml of glacial acetic acid. The reaction was placed under a N$_2$ blanket and heated to reflux for 30 min. The reaction was cooled to room temperature over 45 min, and a red orange solid precipitated from solution. The solid was filtered and washed with 20 ml of glacial acetic acid followed by 2×25 ml of MeOH. The solid was dried at room temperature for 50–60 h under vacuum to yield (3.61 g, 8.12 mmol, 50.7% yield) of

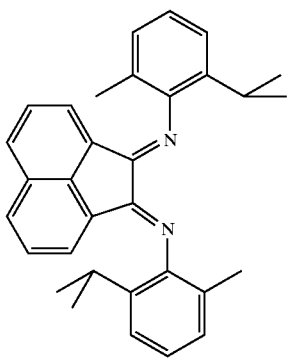

(XII)

$^1$H NMR (500 MHz, CD$_2$Cl$_2$, ppm downfield of TMS): 0.98(d, CHMe$_2$, 6H), 1.21 (d, CHMe$_2$ 6H), 2.06, 2.10 (CH$_3$, anti isomer (major) and syn isomer (minor), 6H), 3.00 (m, CHMe$_2$, 2H), 6.5–8.3 (multiple peaks for aromatic protons, 12H).

EXAMPLE 15

In a dry box, to a one liter RBF, was charged (2.01 g 4.52 mmol) of (XII), (0.697 g, 2.26 mmol) of NiBr$_2$·1,2-dimethoxyethane complex and 26 ml anhydrous methylene chloride. This mixture was stirred for 1.5 h at room temperature. The methylene chloride was then evaporated to leave a brick red solid residue. The solid was collected and charged to a Soxhlet extractor and extracted with pentane for 4 h to remove excess (XII). The resulting greenish solid was dried overnight under vacuum at room temperature to yield (1.17 g, 1.76 mmol, 78.1% yield) of crude

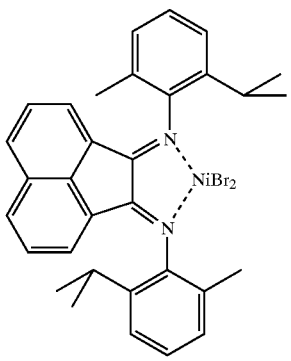

(XIII)

Crude (XIII) (1.17 g) was taken up in 50 ml of anhydrous methylene chloride to which was added 50 ml of anhydrous pentanes. This solution became slightly cloudy. This solution was filtered through a fine fritted funnel into a 125 ml Erlenmeyer flask. The flask was stoppered and allowed to stand overnight at room temperature over which time crystallization occurred. The crystallized solid was filtered and washed with 3×20 ml portions of diethyl ether. This product was dried overnight under vacuum to yield 0.87 g of greenish, finely divided crystalline solid.

The finely divided crystalline solid (0.87 g) was dissolved in 14 ml of anhydrous methylene chloride. To this mixture is added 8.5 g of pentane at once, and then, slowly 2 additional g of pentane to the point of solution turbidity. This solution was allowed to stand overnight at room temperature in the dry box over which time greenish, yellow crystals formed. This solid was filtered and dried for 4 h under vacuum to yield the anti form of (XIII) (0.55 g, 0.83 mmol, 36.7% overall yield). $^1$H NMR (500 MHz, CD$_2$Cl$_2$, ppm downfield of TMS): −15.351 (s, para-ArH, 2H), 2.868 (s, CHMe$_2$, 6H), 3.556 (s, CHMe$_2$, 6H), 5.958 (d, J=4.0 Hz, acenapthene ArH, 2H), 13.177 (broad s, CHMe$_2$, 2H), 16.952 (d, J=6.0 Hz, acenapthene ArH, 2H), 22.525 (s, ArH, 2H), 22.917 (s, ArH, 2H), 23.692 (s, o-CH$_3$, 6H), 25.047 (s, ArH, 2H)

EXAMPLE 16

In a dry box, to an oven dried Schlenk flask, was charged of cyclopentene (10 g, 147 mmol) and anti-(XIII) (0.01 g, 0.015 mmol). The Schlenk flask was sealed and placed in a drybox freezer and chilled over 40 min to −24° C. At −24° C., triethylaluminum (44 µl 1M in hexane, 0.044 mmol) and tris(perfluorophenyl)borane (0.023 g, 0.045 mmol) were added to the flask. The Schlenk flask was immediately resealed and removed from the drybox and placed into a 0° C. bath and mixed for 96 h under N$_2$ during which time a solid precipitate formed. After 96 hrs, 8-hydroxyquinoline (0.02 g, 0.138 mmol) was added to the reaction mixture. The reaction was allowed to stir and warm to room temperature over 20 min after which time the precipitated solid was filtered and washed on the filter with 3×30 ml of MeOH. The filtered solid was dried under vacuum to yield 0.26 g of tan solid.

EXAMPLE 17

In a dry box, to an oven dried Fisher-Porter tube, was charged of cyclopentene (10 g, 147 mmol) and anti-(XIII) (0.01 g, 0.015 mmol), triethylaluminum (44 µl 1M in hexane, 0.044 mmol), and tris(perfluorophenyl)borane (0.023 g, 0.045 mmol). The tube was sealed and immediately removed from the drybox and placed into a 50° C. oil bath for 16 h where it was mixed until it became immobile. After 16 h the Fisher-Porter tube was removed from the oil bath and cleaned thoroughly on the outside and broken to remove the polymer. The polymer was cut into smaller pieces and placed into a Waring® Blender. The blender was charged with 300 ml of MeOH and 8-hydroxyquinoline (0.02 g, 0.138 mmol) and then run at high speed for 30 min. The solid from the blender was collected on a filter and dried under vacuum at room temperature for 2 days to yield 5.65 g of solid. The end of the polymer melting transition occurred at about 325° C.

EXAMPLE 18

In a nitrogen filled dry box, to an oven dried scintillation vial (Vial A) equipped with a magnetic stir bar was added (XIII) (0.0097 g, 0.0146 mmol). To a separate oven dried scintillation vial (Vial B) was added perfluorotriphenyl borane (0.023 g, 0.045 mmol), 10 g of cyclopentene (146.8 mmol) and, 23 µl of triethylaluminum (1.9 M in toluene, 0.045 mmol). After thoroughly mixing vial B to dissolve the borane, the contents of vial B were added to vial A and the mixture was shaken on a Vibramixer® for 168 h at RT. After 168 h of vigorous mixing, 1 ml of methanol was added to the vial to quench the reaction. After 10 min of additional mixing the entire reaction mixture was added to 50 ml of aqueous concentrated HCl/MeOH (3% v/v) and further mixed for 15 min. The solid precipitate was filtered on a medium fritted glass filter and washed with methanol followed by an Irganox 1010®/acetone solution (2% wt/wt). The solid was then dried overnight in vacuo. Net dry weight=3.23 g. The end of the polymer melting transition as measured by DSC (30° C. per minute) occurred at approximately 358° C.

EXAMPLE 19

Preparation of (XV)

Acenathaquinone (15 g, 82 mmol), 2,4,6-trimethylaniline (2.21 g, 16.4 mmol) and formic acid (0.15 g) were combined in 450 mL of anhydrous methanol. The mixture was stirred at room temperature for 60 h under nitrogen, and then evaporated to dryness on a rotoevaporator. The residue was stirred with 450 mL of refluxing ethyl acetate for 30 min and allowed to cool to RT. The mixture was filtered and the filtrate was evaporated to give 4.3 g of red orange solid. This solid was purified by flash chromatography on silica gel with hexane/ethyl acetate (3:1) to give 3.9 g of monoimine (XIV) as an orange crystalline solid (80% yield based on 2,4,6-trimethylaniline).

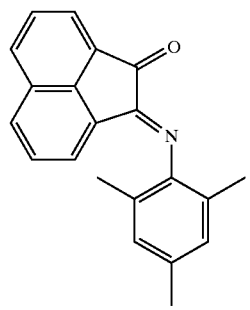

(XIV)

$^1$H NMR (300 MHz, CDCl$_3$): 2.2 (s, o-CH$_3$, 6H); 2.6 (s, p-CH$_3$, 3H); 6.9–8.6 (m, ArH, 8H). The monoimine (XIV) (1.796 g, 6 mmol) was combined with 20 mL of anhydrous methanol and two drops of formic acid in a 500 mL round-bottom flask. o-Phenylaniline (0.20 g, 1.2 mmol) was added to this heterogeneous mixture, and the reaction was stirred at RT for 24 h under a nitrogen atmosphere. The reaction mixture was evaporated to dryness on a rotoevaporator. The orange residue was flash chromatographed on silica gel using a 3:1 mixture of hexane/ethyl acetate (3:1). The desired product (XV)

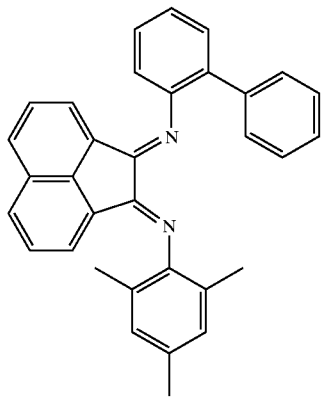

(XV)

(0.285 g yellow solid) was eluted immediately after a faster eluting side-product. It was recrystallized from 5 mL of hexane at −30° C. to give 0.130 g (24% yield based upon monoimine XIV). $^1$H NMR (300 MHz, CD$_2$Cl$_2$): 1.80, 1.98 (s,s o-CH$_3$, 6H); 2.29, 2.37 (s,s, p-CH$_3$, 3H); 6.55–8.2 (m, ArH, 17H). Based on the small extra methyl resonances at 1.80 and 2.29, there appear to be two isomers in a ratio of 85:15.

EXAMPLE 20

Preparation of (XVI)

(XV) (0.050 g, 0.111 mmol) and NiBr$_2$(1,2-dimethoxyethane) (0.034 g, 0.111 mmol) were combined in 1.7 mL of CH$_2$Cl$_2$ in a glass vial and shaken on a vibrating mixer for 24 h in a nitrogen filled drybox. The solution was filtered through a 0.45 μm PTFE membrane filter and the solvent was removed in vacuo to give a rust-brown solid. The product was washed with pentane (2×3 mL) and dried at room temperature in vacuo to give 0.065 g (88% yield). A portion of the sample was recrystallized from toluene/pentane (1:1) by adding pentane slowly to a filtered toluene solution until it became turbid, and then cooling to −30° C. overnight to give dark purple crystals of (XVI).

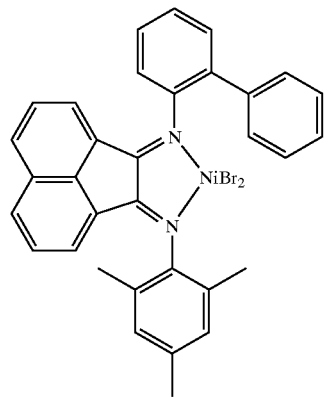

(XVI)

Anal. found (calcd. for C$_{33}$H$_{26}$Br$_2$N$_2$Ni): C, 59.76 (59.24); H, 4.41 (4.19); N, 4.35 (3.92).

EXAMPLE 21

In a nitrogen filled dry box, to an oven dried scintillation vial (Vial A) equipped with a magnetic stir bar was added (XVI) (0.0098 g, 0.0146 mmol). To a separate oven dried scintillation vial (Vial B) was added perfluorotriphenyl borane (0.0225 g, 0.045 mmol), 10 g of cyclopentene (146.8 mmol) and, 23 μl of triethylaluminum (1.9 M in toluene, 0.045 mmol). After thoroughly mixing vial B to dissolve the borane, the contents of vial B were added to vial A. Half of this mixture was shaken on a Vibramixer® for 72 h at RT, and then quenched by addition of 3 mL of MeOH. After 10 min of additional mixing the entire reaction mixture was added to 50 ml of conc. aqueous HCl/MeOH (3% v/v) and mixed for 15 min. The solid precipitate was filtered on a medium fritted glass filter and washed with methanol followed by an Irganox® 1010/acetone solution (2% wt/wt). The solid product was then dried overnight in vacuo. Net dry weight=0.80 gm. The end of the polymer melting transition as measured by DSC (30° C. per min) occurred at approximately 380° C.

EXAMPLE 22

Preparation of (XVII)

In a nitrogen filled dry box to an oven dried scintillation vial was charged mono-imine (XIV) (0.6 g, 2.0 mmol), 20 ml of methanol and 2-isopropyl-6-methyl aniline (0.06 g, 0.40 mmol). The reaction was catalyzed with the addition of 2 drops of formic acid (~0.4 mmol). The mixture was sealed and stirred for 6 days at RT. After 6 days the entire mixture was evaporated to dryness in the presence of 2.0 g of silica gel 60. This silica gel was subjected to column chromatography on silica gel using 75/25 (v/v) hexane/ethyl acetate. The product band was visible in the column and was the first fraction collected. TLC in 75/25 (v/v) hexane/ethyl acetate shows this residue to be a mixture of compounds with one major constituent. This fraction was evaporated to dryness and analyzed by $^1$H NMR which confirmed the product to be a mixture with the major component being the desired ligand (XVII).

(XVII)

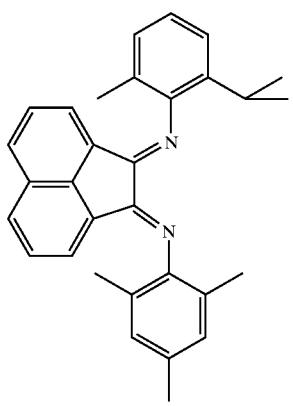

EXAMPLE 23

Preparation of (XVIII)

In a nitrogen filled drybox, to an oven dried scintillation vial were added (XVII) (0.135 g, 0.314 mmol), 4.7 mL of anhydrous methylene chloride and NiBr$_2$(1,2-dimethoxyethane) (0.097 g, 0.314 mmol). The vial was sealed and stirred for 4 h. After 4 h the solvent was removed under vacuum in the drybox. The solid was then washed with 3×10 ml of pentane by slurrying in the scintillation vial, allowing the solid to settle and then decanting the supernatant pentane away via pipette. The product (XVIII) was dried overnight in vacuo.

(XVIII)

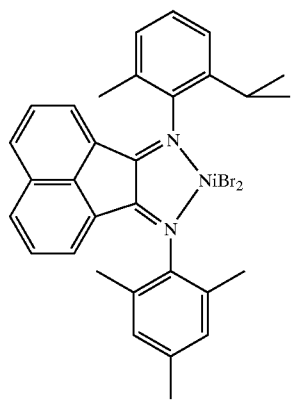

EXAMPLE 24

In an nitrogen filled dry box, to an oven dried scintillation vial were added (XVIII) (0.0094 g, 0.0145 mmol), perfluorotriphenyl borane (0.023 g, 0.045 mmol) and cyclopentene (10 g, 146.8 mmol). This mixture was shaken vigorously for 10 min to dissolve the borane.

After borane solvation, 44 μl of triethylaluminum was added (1.0 M in hexane 0.044 mmol) and the mixture was further shaken for 30 min where-by a slight pink haze began to develop. At this point a 5 gm aliquot (50% of the mixture) was removed and placed in a separate scintillation vial and mixed by shaking for 168 h. The mixture was then quenched by the addition of 1 mL of MeOH. After 10 min of additional mixing the entire reaction mixture was added to 50 ml of concentrated aqueous HCl/MeOH (3% v/v) and further mixed for 15 min. The solid precipitate was filtered on a medium fritted glass filter and washed with 3×20 mL of methanol followed by 20 ml of Irganox® 1010/acetone solution (2% wt/wt). The solid was then dried overnight in the drybox in vacuo. Net dry weight=1.19 g. The end of the polymer melting transition as measured by DSC (30° C. per minute) occurred at approximately 350° C.

EXAMPLE 25

In a nitrogen filled drybox, to an oven dried scintillation vial were added in order: (XIII) (0.0086 g), perfluorotriphenyl borane (0.020 g), cyclopentene (6.22 g), 3-ethylcyclopentene (3.78 g), and triethylaluminum (39.2 μl of a 1M solution in hexanes). The mixture was shaken at room temperature on a vibrating mixer for 15.5 h and then quenched by the addition of 0.045 g 8-hydroxyquinoline dissolved in toluene. The quenched mixture was poured into 150 mL of MeOH and stirred for 3 days. The mixture was filtered and the solid product was collected on a medium fritted glass filter and washed on the filter with 3×30 mL of additional MeOH. The solid product was dried on a high vacuum line at 111° C. for 5 hours. Yield is 1.98 g. $^{13}$C NMR shows that the product contains about 5 mole % 3-ethylcyclopentene. DSC (30° C./min) shows an end of melting point at about 245° C. This can be compared to an end of melting point of 358° C. for homopolycyclopentene made with this catalyst at RT (Example 18).

EXAMPLE 26

Norcamphorquinone was prepared by oxidation of norcamphor using selenium dioxide following the procedure of K. Alder, et. al. Liebigs Ann. Chem. 593, 23 (1955) and used without further purification due to its instability.

Norcamphorquinone (4.2 g, 34 mmol) and 2-isopropyl-6-methylaniline (14.3 g, 96.2 mmol) were dissolved in 40 mL methanol. The solution was stirred at room temperature for 2 days. Thin-layer chromatography (silica, 50% ethyl acetate/hexanes) showed only two spots near the elution front. The solution was evaporated on a rotoevaporator to give a viscous brown oil, which was eluted through a column of basic alumina using dichloromethane to remove dark-colored material. The solution was evaporated on a rotoevaporator to give a crude orange-yellow oil, bis(2-isopropyl-6-methylphenylimino)norbornane, (2,6-iPrMePhN)$_2$NB, which was dried under vacuum.

EXAMPLE 27

Inside a dry box, crude (2,6-iPrMePhN)$_2$NB from Example 25 (0.63 g, 1.6 mmol), and (1,2-dimethoxyethane)nickel(II) bromide (0.50 g, 1.6 mmol) were combined in 50 mL dichloromethane and stirred overnight. The solution was diluted with petroleum ether to precipitate a brown powder. The powder was collected by vacuum filtration, dissolved in minimal dichloromethane (20 mL), and diluted sequentially with petroleum ether to induce recrystallization. The crystals were collected by vacuum filtration and dried under vacuum to give 0.06 g of [(2,6-iPrMePhN)$_2$NB]NiBr$_2$.

EXAMPLE 28

A sample of the oil from Example 1 was dissolved in methanol and diluted dropwise with water. An oil separated from the solution. The oil was taken up in 200 mL hexanes and extracted repeatedly with water. The solution was evaporated on a rotoevaporator and the resulting oil was dried under vacuum. The $^1$H NMR (500 MHz, CDCl$_3$) spectrum of the oil indicated a mixture of [(2,6-iPrMePhN)$_2$NB and residual excess 2-isopropyl-6-methylaniline.

A sample of this oil (0.94 g) was dissolved in 15 mL glacial acetic acid and treated with 1.5 mL acetic anhydride. Nickel(II) bromide (0.44 g, 2.0 mmol) was added and the mixture was stirred for several days. The solids were collected by vacuum filtration, washed two times with acetic acid to give colorless washings, washed two times with hexanes, and dried under vacuum. The solids were dissolved in dichloromethane and the solution was filtered to leave behind a dark insoluble material. The solution was diluted with sufficient hexane to precipitate the solids. After filtration, a second crop was obtained by concentrating the filtrate. The combined solids were dissolved in minimal dichloromethane. The solution was slowly diluted with hexanes to induce recrystallization. The red-brown crystals were collected by filtration, washed with hexanes, and dried under vacuum to give 0.59 g (48%) of [(2,6-iPrMePhN)$_2$NB]NiBr$_2$.

EXAMPLE 29

Inside a dry box, a sample of [(2,6-iPrMePhN)$_2$NB]NiBr$_2$ from Example 27 (0.0070 g, 0.012 mmol) was weighed out into a glass vial. Cyclopentene (11 mL, 10,000 equivalents/Ni) was added by syringe. The polymerization was initiated with stirring by adding a 1.9 M solution of triethylaluminum in toluene (0.040 mL, 6 equivalents/Ni) and tris (pentafluorophenyl)borane (0.040 g, 6 equivalents/Ni). Sufficient polymer precipitated over the course of polymerization that stirring was not maintained for the entire time. After 7 days, the polymerization was quenched by adding 8-hydroxyquinoline (57 mg, 0.39 mmol) in toluene. The polymer was dispersed in a blender with 250 mL toluene. The yellow-green catalyst residues were extracted by diluting with 250 mL methanol. The polymer was filtered off and washed with methanol until the filtrate was colorless, then treated with a 0.5% solution of Irganox® 1010 in acetone. The polymer was dried at 120° C. in a nitrogen-purged vacuum oven to give 3.49 g (4400 turnovers/Ni) polycyclopentene. DSC (0–350° C., 10° C./min, second heat): $T_g$ 101° C., $T_m$ (onset) 114° C., $T_m$ (peak) 232° C., $T_m$ (end) 324° C., $H_f$ 35 J/g. GPC (1,2,4-TCB, 135° C., IR detection, polyethylene calibration): $M_n$ 31,400, $M_w$ 59,400, $M_w/M_n$ 1.90, $M_z$ 97,300, $M_z/M_w$ 1.64.

EXAMPLE 30

Inside a dry box, a sample of [(2,6-iPrMePhN)$_2$NB]NiBr$_2$ from Example 28 (0.015 g, 0.025 mmol) was weighed out into a glass vial. Cyclopentene (22 mL, 10,000 equivalents/Ni) was added by syringe. The polymerization was initiated with stirring by adding a 1.9 M solution of triethylaluminum in toluene (0.079 mL, 6 equivalents/Ni) and tris (pentafluorophenyl)borane (0.077 g, 6 equivalents/Ni). Sufficient polymer precipitated over the course of polymerization that stirring was not maintained for the entire time. After 7 days, the polymer was dispersed in a blender with 200 mL toluene and 8-hydroxyquinoline (57 mg, 0.39 mmol). The yellow-green catalyst residues were extracted by diluting with 200 mL methanol. The polymer was filtered off and washed with methanol until the filtrate was colorless, then treated with a 0.5% solution of Irganox® 1010 in acetone. The polymer was dried at 120° C. in a nitrogen-purged vacuum oven to give 4.86 g (2900 turnovers/Ni) polycyclopentene. DSC (0–350° C., 10° C./min, second heat): $T_g$ 105° C., $T_m$ (onset) 124° C., $T_m$ (peak) 256° C., $T_m$ (end) 329° C., $H_f$ 37 J/g. The polymer melting point was too high to obtain a melt index or perform the molecular weight analysis.

EXAMPLE 31

Inside a dry box, a sample of [(2,6-iPrMePhN)$_2$NB]NiBr$_2$ from Example 28 (0.016 g, 0.026 mmol) and tris (pentafluorophenyl)borane (0.077 g, 6 equivalents/Ni) were weighed out into a glass vial. Cyclopentene (22 mL, 10,000 equivalents/Ni) was added by syringe. The polymerization was initiated with stirring by adding a 1.9 M solution of triethylaluminum in toluene (0.079 mL, 6 equivalents/Ni). Sufficient polymer precipitated over the course of polymerization such that stirring was not maintained for the entire time. After 7 days, the polymer was dispersed in a blender with 200 mL toluene and 8-hydroxyquinoline (60 mg, 0.39 mmol). The yellow-green catalyst residues were extracted by diluting with 200 mL methanol. The polymer was filtered off and washed with methanol until the filtrate was colorless, then treated with a 0.5% solution of Irganox® 1010 in acetone. The polymer was dried at 120° C. in a nitrogen-purged vacuum oven to give 9.28 g (5200 turnovers/Ni) polycyclopentene. DSC (0–350° C., 10° C./min, second heat): $T_g$ 84° C., $T_m$ (onset) 114° C., $T_m$ (peak) 241° C., $T_m$ (end) 324° C., $H_f$ 29 J/g.

EXAMPLE 32

Inside a dry box, a sample of [(2,6-iPrMePhN)$_2$NB]NiBr$_2$ from Example 28 (0.054 g, 0.089 mmol) was charged to a glass bottle. A 60 mL portion of a solution of cyclopentene (80 mL, 10,000 equivalents/Ni) in 120 mL 1,2,4-trichlorobenzene was added to the bottle. The polymerization was initiated with stirring by first adding tris (pentafluorophenyl)borane (0.28 g, 6 equivalents/Ni) followed by a 1.9 M solution of triethylaluminum in toluene (0.30 mL, 6 equivalents/Ni). After 30 min, the solution was diluted with the remaining cyclopentene solution. After 7 days, the dark brown solution would gel upon standing. After 14 days, the polymer was dispersed in a blender with 250 mL toluene and 8-hydroxyquinoline (0.42 g, 0.39 mmol). The yellow-green catalyst residues were extracted by diluting with 250 mL methanol. The polymer was filtered off and washed with methanol three times until the filtrate was colorless, then treated with a 0.5% solution of Irganox® 1010 in acetone. The polymer was dried at 120° C. in a nitrogen-purged vacuum oven to give 41.64 g (6800 turnovers/Ni) polycyclopentene. DSC (0–350° C., 10° C./min, second heat): $T_g$ 100° C., $T_m$ (onset) 117° C., $T_m$ (peak) 255° C., $T_m$ (end) 328° C., $H_f$ 38 J/g.

What is claimed is:

1. A process for the polymerization of one or more olefins selected from the group consisting of 3-methylcyolopentene, 4-methylcyclopentene, 3-ethylcyclopetnene and 3-cyclopentylcyclopentene, by contacting, at a temperature of −100° C. to about 200° C., said olefin with an olefin polymerization catalysts system containing a nickel or palladium complex of a compound of the formula

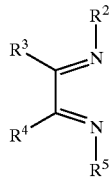

and optionally other cocatalysts, herein $R^2$ and $R^5$ are each independently hydrocarbyl or substituted hydrocarbyl, provided that the carbon atom bound to the imino nitrogen atom has at least two carbon atoms bound to it;

$R^3$ and $R^4$ are each independently hydrogen, hydrocarbyl, substituted hydrocarbyl, or $R^3$ and $R^4$ taken together are hydrocarbylene or substituted hydrocarbylene to form a carboxyclic ring.

* * * * *